US008670839B2

(12) United States Patent
Carbunaru et al.

(10) Patent No.: US 8,670,839 B2
(45) Date of Patent: Mar. 11, 2014

(54) IMPLANTABLE SYSTEM WITH IMPROVED RF TOLERANCE

(71) Applicant: Boston Scientific Neuromodulation Corporation, Valencia, CA (US)

(72) Inventors: Rafael Carbunaru, Valley Village, CA (US); Salomo Murtonen, Pasadena, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 13/712,779

(22) Filed: Dec. 12, 2012

(65) Prior Publication Data

US 2013/0150938 A1    Jun. 13, 2013

Related U.S. Application Data

(60) Provisional application No. 61/569,419, filed on Dec. 12, 2011.

(51) Int. Cl.
  *A61N 1/00* (2006.01)
(52) U.S. Cl.
  USPC ......................................... 607/116
(58) Field of Classification Search
  USPC .................................. 607/116, 112
  See application file for complete search history.

(56) References Cited

U.S. PATENT DOCUMENTS

| 6,181,969 | B1 | 1/2001 | Gord |
| 6,516,227 | B1 | 2/2003 | Meadows et al. |
| 6,609,029 | B1 | 8/2003 | Mann et al. |
| 6,609,032 | B1 | 8/2003 | Woods et al. |
| 6,741,892 | B1 | 5/2004 | Meadows et al. |
| 7,244,150 | B1 | 7/2007 | Brase et al. |
| 7,672,734 | B2 | 3/2010 | Anderson et al. |
| 7,761,165 | B1 | 7/2010 | He et al. |
| 7,949,395 | B2 | 5/2011 | Kuzma |
| 7,974,706 | B2 | 7/2011 | Moffitt et al. |
| 8,175,710 | B2 | 5/2012 | He |
| 2005/0165465 | A1 | 7/2005 | Pianca et al. |
| 2007/0150036 | A1 | 6/2007 | Anderson |
| 2009/0149934 | A1* | 6/2009 | Ameri et al. ............... 607/122 |
| 2011/0043297 | A1* | 2/2011 | Stevenson et al. ........... 333/12 |
| 2012/0130461 | A1* | 5/2012 | Olsen et al. ............... 607/116 |
| 2012/0157811 | A1* | 6/2012 | Bartels et al. ............... 600/374 |

* cited by examiner

*Primary Examiner* — Robert N Wieland
(74) *Attorney, Agent, or Firm* — Frommer Lawrence & Haug LLP; Bruce E. Black (57) ABSTRACT

One embodiment is an implantable lead including a lead body having a proximal end and a distal end; multiple electrodes disposed along the distal end of the lead body; multiple terminal contacts disposed along the proximal end of the lead body; multiple stimulation conductors extending along the lead body and electrically coupling the electrodes to the terminal contacts; at least one diversionary terminal contact disposed along the proximal end of the lead body; and at least one diversionary conductor extending at least partially along the length of the lead body and coupled to the at least one diversionary terminal contact and not coupled to any of the electrodes. The at least one diversionary conductor is configured and arranged to capacitively couple to the stimulation conductors.

20 Claims, 6 Drawing Sheets

IMPLANTABLE SYSTEM WITH IMPROVED RF TOLERANCE

CROSS-REFERENCE TO RELATED APPLICATIONS

This application claims the benefit under 35 U.S.C. §119 (e) of U.S. Provisional Patent Application Ser. No. 61/569,419 filed on Dec. 12, 2011, which is incorporated herein by reference.

FIELD

The present invention is directed to implantable electrical stimulation systems and methods of making and using the systems. The present invention is also directed to implantable electrical stimulation leads having radio frequency (RF) compatibility, and implantable electrical stimulation systems that include the lead, as well as methods of making and using the leads and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

Conventional implanted electrical stimulation systems may be incompatible with magnetic resonance imaging (MRI) due to the large radio frequency (RF) pulses used during MRI. The RF pulses can generate transient signals in the conductors and electrodes of an implanted lead. These signals can have deleterious effects including, for example, unwanted heating of the tissue or damage to electronic components in the control module.

BRIEF SUMMARY

One embodiment is an implantable lead including a lead body having a proximal end and a distal end; multiple electrodes disposed along the distal end of the lead body; multiple terminal contacts disposed along the proximal end of the lead body; multiple stimulation conductors extending along the lead body and electrically coupling the electrodes to the terminal contacts; at least one diversionary terminal contact disposed along the proximal end of the lead body; and at least one diversionary conductor extending at least partially along the length of the lead body and coupled to the at least one diversionary terminal contact and not coupled to any of the electrodes. The at least one diversionary conductor is configured and arranged to capacitively couple to the stimulation conductors.

Another embodiment is an implantable stimulation system that includes the implantable lead described above and a control module. The control module includes a housing, stimulation electronics disposed within the housing of the control module, a connector configured and arranged to receive the proximal end of the lead, multiple conductive contacts disposed within the connector and configured and arranged for contacting the terminal contacts of the lead and coupling the lead to the stimulation electronics, and at least one diversionary conductive contact disposed within the connector and configured and arranged for contacting the at least one diversionary terminal contact of the lead.

Yet another embodiment is an implantable stimulation system that includes the implantable lead described above, an implantable lead extension, and a control module. The implantable lead extension has a proximal end and a distal end and includes a connector disposed at the distal end of the lead extension and configured and arranged to receive the proximal end of the lead, multiple conductive contacts disposed within the connector and configured and arranged for contacting the terminal contacts of the lead, at least one diversionary conductive contact disposed within the connector and configured and arranged for contacting the at least one diversionary terminal contact of the lead, multiple terminal contacts disposed along the proximal end of the lead extension; at least one diversionary terminal contact disposed along the proximal end of the lead extension, and multiple conductors extending along the lead extension and electrically coupling the conductive contacts to the terminal contacts and the at least one diversionary conductive contact to the at least one diversionary terminal contact. The control module includes stimulation electronics disposed within the control module, a connector configured and arranged to receive the proximal end of the lead extension, multiple conductive contacts disposed within the connector and configured and arranged for contacting the terminal contacts of the lead extension and coupling the lead and lead extension to the stimulation electronics, and at least one diversionary conductive contact disposed within the connector and configured and arranged for contacting the at least one diversionary terminal contact of the lead extension.

It is to be understood that both the foregoing general description and the following detailed description are exemplary and explanatory only and are not restrictive of the invention, as claimed.

BRIEF DESCRIPTION OF THE DRAWINGS

Non-limiting and non-exhaustive embodiments of the present disclosure are described with reference to the following drawings. In the drawings, like reference numerals refer to like parts throughout the various figures unless otherwise specified.

For a better understanding of the present disclosure, reference will be made to the following detailed description, which is to be ready in association with the accompanying drawings, wherein.

Corresponding reference characters indicate corresponding components throughout the several views of the drawings.

DETAILED DESCRIPTION

The present disclosure is directed to the area of implantable electrical stimulation systems and methods of making and using the systems. The present invention is also directed to implantable electrical stimulation leads and lead extensions having RF compatibility, and implantable electrical stimulation systems that include the lead, as well as methods of making and using the leads and electrical stimulation systems.

Suitable implantable electrical stimulation systems include, but are not limited to, a least one lead with one or more electrodes disposed on a distal end of the lead, and one or more terminal contacts disposed on one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,244,150; 7,672,734; 7,761,165; 7,949,395; 7,974,706; and 8,175,710; U.S. Patent Application Publication Nos. 2005/0165465 and 2007/0150036, all of which are incorporated by reference.

It is often desirable to make an implantable electrical stimulation system compatible with magnetic resonance imaging (MRI). MRI is often used as a diagnostic imaging procedure. An MRI procedure includes the use of large radio-frequency (RF) fields which may interact with an implantable device. One particular type of RF interaction is the generation of current in the conductors of an implanted lead in response to the RF field. Such currents may be conducted along the conductors and into the implantable pulse generator (IPG) or surrounding tissue. Typically, neurostimulation leads contain conductors (e.g., wires) that connect proximally to the IPG, and distally to the electrodes. These conductors in the lead can act as antennas in which current can be induced by RF energy, and that energy can be transferred to the IPG, where it can affect the behavior of the IPG and even result in permanent damage to electronic components of the IPG. It is desirable to include design features in these devices to make them better capable of tolerating exposure to the RF fields used in an MRI procedure without damaging the components of the IPG.

It will be understood that, although embodiments of the present invention will be described with reference to spinal cord stimulation, the devices described herein may be utilized in other stimulation systems that can be used to stimulate other nerves, organs, and tissues, such as the brain, urinary system, or any other organ, nerve, or tissue that might benefit from such stimulation.

Figure 1:
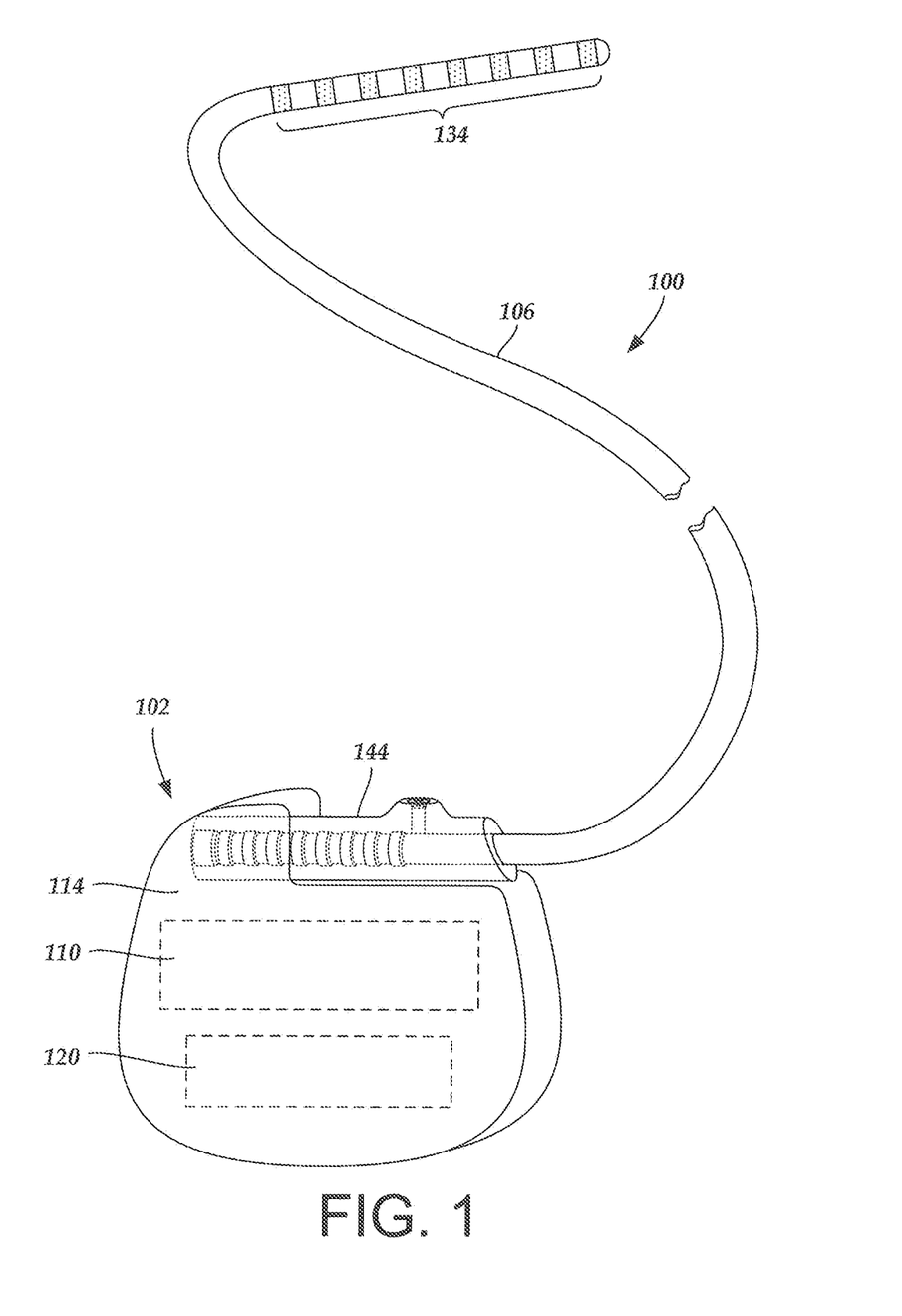
FIG. 1 is a schematic perspective view of one embodiment of an electrical stimulation system, according to the invention.

FIG. 1 illustrates schematically one embodiment of an electrical stimulation system 100. The electrical stimulation system includes a control module (e.g., a stimulator or implantable pulse generator) 102 and at least one lead 106 ("lead") coupled to the control module 102. Each lead 106 typically includes an array of electrodes 134. The control module 102 typically includes an electronic subassembly 110 and an optional power source 120 disposed in a sealed housing 114. The control module 102 typically includes a connector 144 into which the proximal end of the lead 106 can be inserted to make an electrical connection between the control module and the lead via conductive contacts on the control module 102 and terminal contacts (e.g., 210 in FIG. 2A and FIG. 2B) on the lead 106. In at least some embodiments, a lead is isodiametric along a longitudinal length of the lead 106. In other embodiments, the lead may include a paddle at its distal end with electrodes disposed on the paddle.

The electrical stimulation system or components of the electrical stimulation system, including the lead 106 and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. The number of electrodes 134 in the array of electrodes 134 may vary. For example, there can be two, four, six, eight, ten, twelve, fourteen, sixteen, or any other number of electrodes 134.

Terminal contacts (e.g., 210 in FIG. 2A and FIG. 2B) are typically disposed at the proximal end of the lead 106 for connection to corresponding conductive contacts (e.g., 214 in FIGS. 2A and 240 of FIG. 2B) in the connector (e.g., 144 in FIGS. 1-2A and 222 and 250 of FIG. 2B) disposed on, for example, the control module 102 (or to conductive contacts in a connector of a lead extension, an operating room cable, or an adaptor). Stimulation conductors couple the terminal contacts of a lead to the electrodes of the lead. In at least some embodiments, the number of electrodes can equal the number of terminal contacts and the each electrode is coupled to a different terminal contact. In other embodiments, more than one electrode may be coupled to each terminal contact.

Figure 2A:
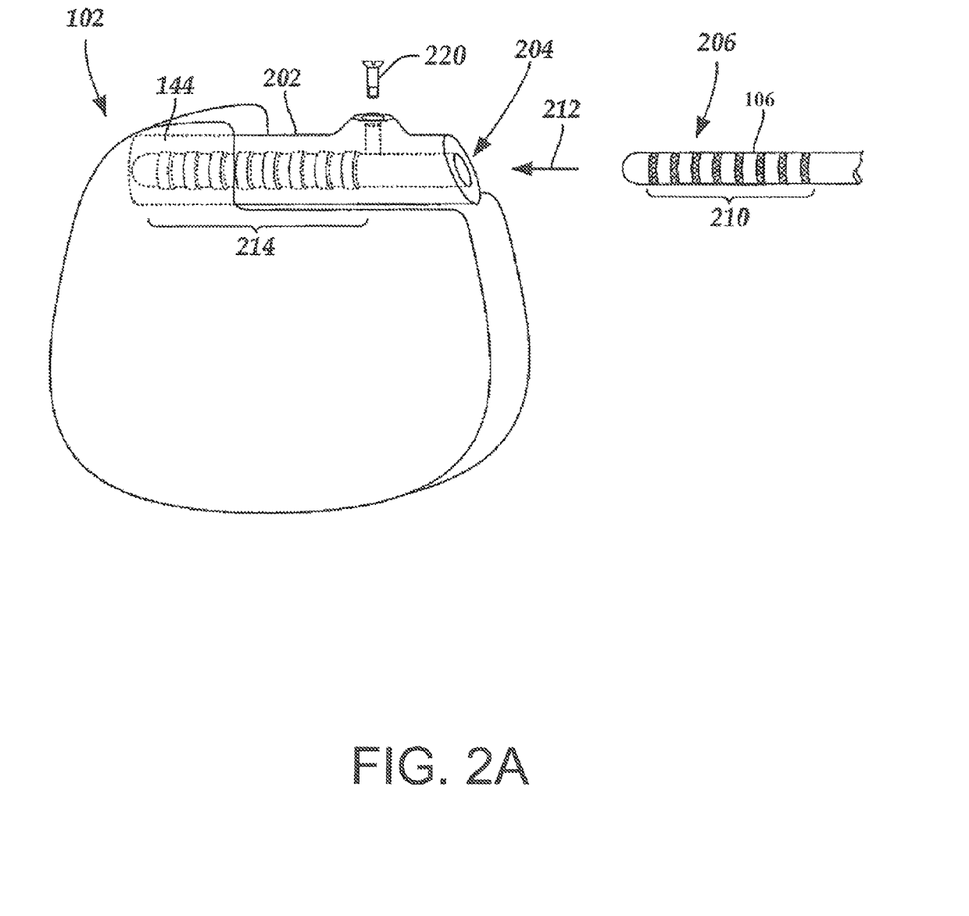
FIG. 2A is a schematic perspective view of one embodiment of a proximal portion of a lead and a control module of an electrical stimulation system, according to the invention.

In at least some embodiments, the lead is coupled to a connector disposed on the control module. In FIG. 2A, a lead 106 is shown configured and arranged for insertion to the control module 102. The connector 144 includes a connector housing 202. The connector housing 202 defines at least one port 204 into which a proximal end 206 of the lead 106 with terminal contacts 210 can be inserted, as shown by directional arrow 212. The connector housing 202 also includes a plurality of conductive contacts 214 in the port 204. When the lead 106 is inserted into the port 204, the conductive contacts 214 are aligned with the terminal contacts 210 on the lead 106 to electrically couple the control module 102 to the electrodes (134 of FIG. 1) disposed at a proximal end 206 of the lead 106. In at least some embodiments, the connector includes a retention fastener 220 that can fastener the lead to the connector once the lead is inserted to prevent the lead from being withdrawn. In at least some embodiments, the lead may include a metal retention sleeve against which the retention fastener can be tightened.

Figure 2B:
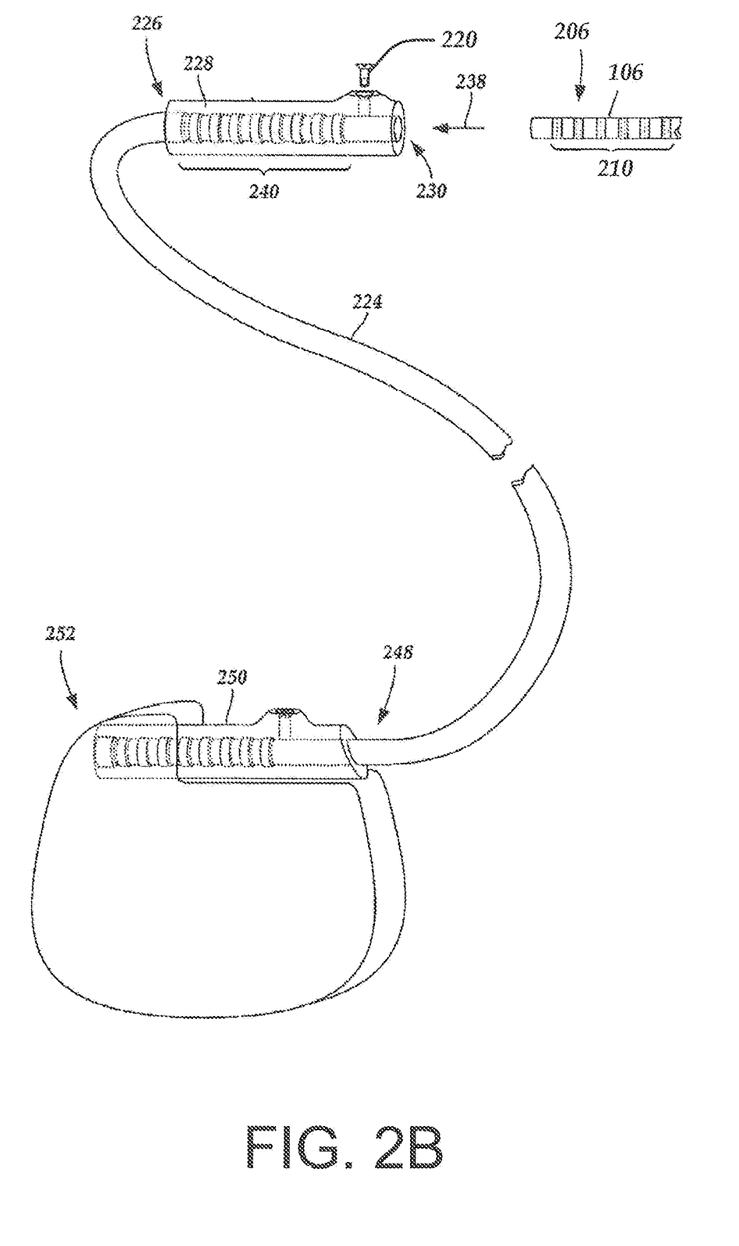
FIG. 2B is a schematic perspective view of one embodiment of a proximal portion of a lead and a lead extension of an electrical stimulation system, according to the invention.

In FIG. 2B, a connector 222 is disposed on a lead extension 224. The connector 222 is shown disposed at an end 226 of the lead extension 224. The connector 222 includes a connector housing 228. The connector housing 228 defines at least one port 230 into which a proximal end 206 of a lead 106 with terminal contacts 210 can be inserted, as shown by directional arrow 238. The connector housing 228 also includes a plurality of conductive contacts 240. When the lead 106 is inserted into the port 230, the conductive contacts 240 disposed in the connector housing 228 can be aligned with the terminal contacts 210 on the lead 106 to electrically couple the lead extension 224 to the electrodes (134 of FIG. 1) disposed at a distal end (not shown) of the lead 106.

In at least some embodiments, the proximal end of a lead extension is similarly configured and arranged as a proximal end of a lead. The lead extension 224 may include a plurality of conductors that electrically couple the contacts in the connector on the distal end of the lead extension to terminal contacts on the proximal end 248 of the lead extension 224. The proximal end 248 of the lead extension 224 is configured and arranged for insertion into a connector disposed in a control module. As an example, in FIG. 2B, the proximal end 248 of the lead extension 224 is inserted into a connector 250 disposed in a control module 252.

The lead includes the stimulation conductors 306 (see, e.g., FIG. 3A) extending from the terminal contacts (e.g., 210 in FIG. 2A and FIG. 2B) to the electrodes 134. Typically, one or more electrodes 134 are electrically coupled to a terminal contact (e.g., 210 in FIG. 2A and FIG. 2B). In at least some embodiments, each terminal contact (e.g., 210 in FIG. 2A and FIG. 2B) is only connected to one electrode 134.

A lead can include one or more additional conductors that are not coupled between an electrode and terminal contact. These additional conductor(s) can be arranged to divert at least some of the current induced in the lead by the RF field away from tissue or sensitive electrical components in the control module. For example, one or more additional diversionary conductors may be arranged to capacitively couple to the stimulation conductors stretching from the electrodes to the terminal contacts to reduce the flow of RF-induced current on these stimulation conductors. The one or more diversionary conductors can be coupled, for example, to a terminal contact that is directly or indirectly coupled to a conductive portion of the housing of the control module, or some other arrangement, to allow diversion and dissipation of the RF-induced current to avoid or reduce the potential for damage to sensitive electronic components of the control module.

Figure 3A:
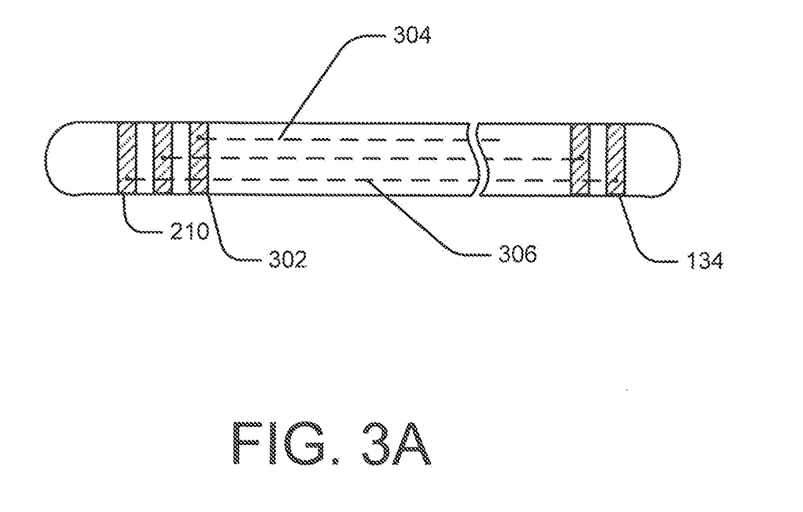
FIG. 3A is a schematic side view of one embodiment of a lead, according to the invention.
Figure 3B:
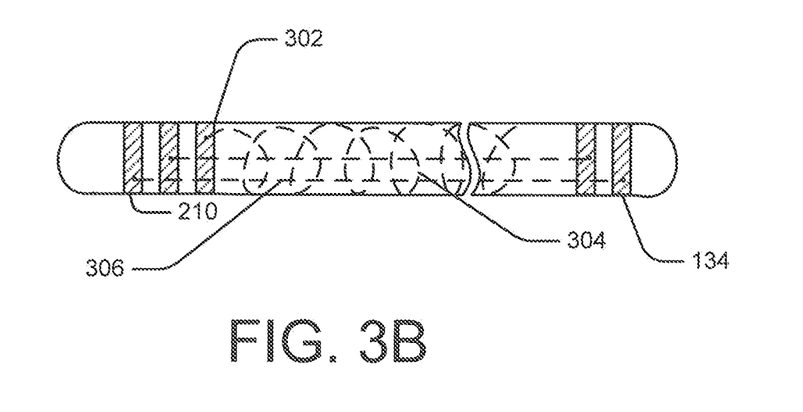
FIG. 3B is a schematic side view of another embodiment of a lead, according to the invention.

FIGS. 3A and 3B illustrate a cross section of the lead 106. In addition, to the terminals 210, the lead 106 includes one or more diversionary terminal contacts 302 disposed on the proximal end of the lead 106. One or more diversionary conductors 304 extend from the one or more diversionary terminal contacts 302 towards the distal end of the lead 106. The distal end of a diversionary conductor 304 is not attached to any electrode 134 or to any of the stimulation conductors 306 disposed between the electrodes 134 and terminal contacts 210.

The objective of the diversionary conductor is to divert some (or most) of the RF-induced current into the one or more diversionary conductors instead of through the stimulation conductors. This will reduce or prevent RF-induced current from passing into tissue through the electrodes 134 or into the electronic components of the control module through the terminal contacts 210. Although not wanting to be bound to any particular theory, it is thought that the diversionary conductors 304 can be disposed and arranged to capacitively couple, or otherwise divert, RF energy from the stimulation conductors 306 into the diversionary conductors. In at least some embodiments, the diversionary conductors are arranged to present a lower impedance to the RF energy at the MRI frequency than the stimulation conductors. Lower impedance can be achieved by, for example, reducing the total length of wire, reducing the path of the wire, using materials that are more conducting (less resistive) or achieving a self-resonant behavior with smaller net impedance for RF currents at MRI RF frequencies (for example approximately 64 MHz for 1.5T MR imagers, approximately 128 MHz for 3T MR imagers, and corresponding RF frequencies known to those familiar with these topics for MR imagers with smaller or higher magnetic field strength).

The diversionary conductors 304 may extend through substantially the entire length of the lead 106 or along only a portion of the length of the lead. The diversionary conductors 304 can be of any suitable length. However, to facilitate coupling of the RF power into the diversionary conductors 304, the length of the diversionary conductor 304 may be selected to correspond to (or close to) an integer multiple of one-half of the wavelength of an expected MRI RF frequency. Examples of expected MRI RF frequencies include, but are not limited to, 64 MHz, 85 MHz, and 128 MHz. The matching of length of the diversionary conductor 304 to an integer multiple of half the wavelength of the RF frequency may enable increasing coupling of the RF energy into the diversionary conductors. In some embodiments, two or more diversionary conductors 304 may be included in the lead and have different lengths that each correspond to an integer multiple of half the wavelength of different RF frequencies associated with MRI procedures.

In at least some embodiments, as shown in FIGS. 3A and 3B, a diversionary conductor 304 is in close proximity to one or more of the stimulation conductors 306 to facilitate capacitive coupling with the stimulation conductors. The diversionary conductor 304 may be disposed on the surface of the lead or within the lead. The diversionary conductor is generally insulated to reduce current leakage or short-circuiting. The diversionary conductor may be oriented in any suitable arrangement relative to the stimulation conductors. For example, as illustrated in FIG. 3A, the diversionary conductor may be parallel to the stimulation conductors. In other embodiments, as illustrated in FIG. 3B, the diversionary conductor may be looped around one or more (or even all) of the stimulation conductors or wound around one or more (or even all) of the stimulation conductors in a helical manner. In embodiments, with multiple diversionary conductors, each of the diversionary conductors may be arranged similarly or in different manner (e.g., one or more diversionary conductors extending straight and one or more diversionary conductors being looped or helically wound.) In some embodiments, a diversionary conductor may include both straight and looped/wound portions in any suitable combination. In at least some embodiments, the diversionary conductors may be multi-filar wires. The multiple filars can run together (e.g., along the same path) or separate (e.g., along different paths).

In embodiments with multiple diversionary conductors, the diversionary conductors may be of the same or different lengths and orientations. The diversionary conductors may also be present at the same layer, radial position, or circumferential position, or at different layers, radial positions, or circumferential positions (or any combination thereof) of the lead structure.

Materials with high dielectric constant may be disposed between the diversionary conductor(s) and stimulation conductors to promote capacitive coupling. Such materials can include, but are not limited to, glass, plastics, such as polyethylene or polyvinylchloride, ceramics, and liquid dielectrics, such as mineral oils and organic oils. Vacuum or air may also be used as dielectric materials of low permittivity to reduce capacitive coupling between the stimulation conductors. Fluid or vacuum dielectrics may be applicable when the stimulation conductors or diversionary conductors are encased in a lumen or cavity.

Diversionary conductors and diversionary terminal contacts such as those illustrated in FIGS. 3A and 3B can be provided in lead extensions. Such diversionary contacts may not be coupled to contacts on the distal end of the lead extension.

Figure 4:
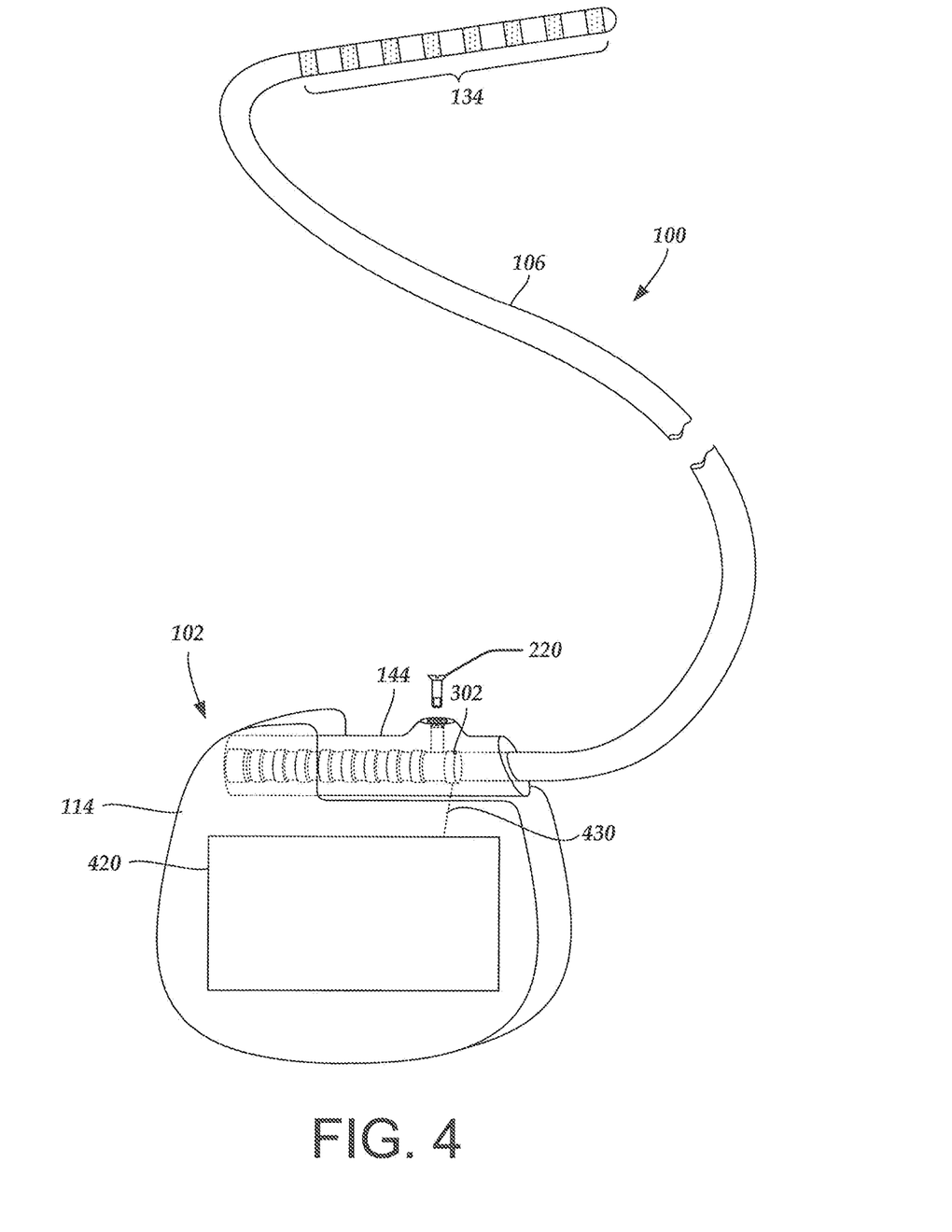
FIG. 4 Is a schematic perspective view of another embodiment of an electrical stimulation system, according to the invention.

FIG. 4 is a schematic cross-sectional view of a control module and lead. One or more diversionary terminal contacts 302 present at the proximal end of the lead 106 are connected to the control module through conductive contacts in the control module. In alternative embodiments, the diversionary terminal contact(s) present at the proximal end of lead may be in conductive communication with one or more conductive contacts at the distal end of a lead extension. This particular conductive contact(s) of the lead extension are coupled by one or more conductors to one or more diversionary terminal contacts as the proximal end of the lead extension. The proximal end of lead extension is inserted into a connector on the control module with the diversionary terminal contact(s) on the lead extension coupled to conductive contacts in the control module. Such an arrangement allows the current generated in the diversionary conductors of the lead to flow through the lead extension to the control module.

The diversionary terminal contacts of the lead or lead extension may be directly or capacitively coupled to the conductive contacts of the control module. In at least some embodiments, the diversionary terminal contact(s) of the lead or lead extension is coupled to a conductive contact(s) of the control module to direct the current generated in the diversionary conductor(s) of the lead or lead extension away from the sensitive electronic components of the control module and allow the current to be dissipated. For example, this current from the diversionary conductors, coupled through one or more conductive contacts in the control module, may be directed via a conductor 430 to a conductive portion 420 on the exterior of the housing of the control module as illustrated in FIG. 4. In these embodiments, the current may be dissipated into surrounding tissue. Preferably, the surface area of the conductive portion of the housing of the control module is relatively large to reduce or prevent substantial heating of the adjacent tissue as the current is dissipated. In other embodiments, the current may be directed to one or more components (e.g., components 422 in FIG. 5), within the control module or outside the control module (such as a load external to the control module), that can be used to dissipate or store the energy or the current can be directed to a ground.

In some embodiments, the termination of the diversionary conductors and the conductive contacts of the control module and related components can be arranged to provide a good impedance match, particularly at one or more expected MRI RF frequencies, to promote power transfer into those diversionary conductors and away from the stimulation conductors and sensitive electronics of the control module. In some embodiments, the conductive contacts may be coupled to circuitry that presents an impedance that is equal or substantially similar (e.g., within at least 50%, at least 20%, at least 10%, or at least 5%) to the complex conjugate of the impedance of the diversionary conductor(s).

Figure 5:
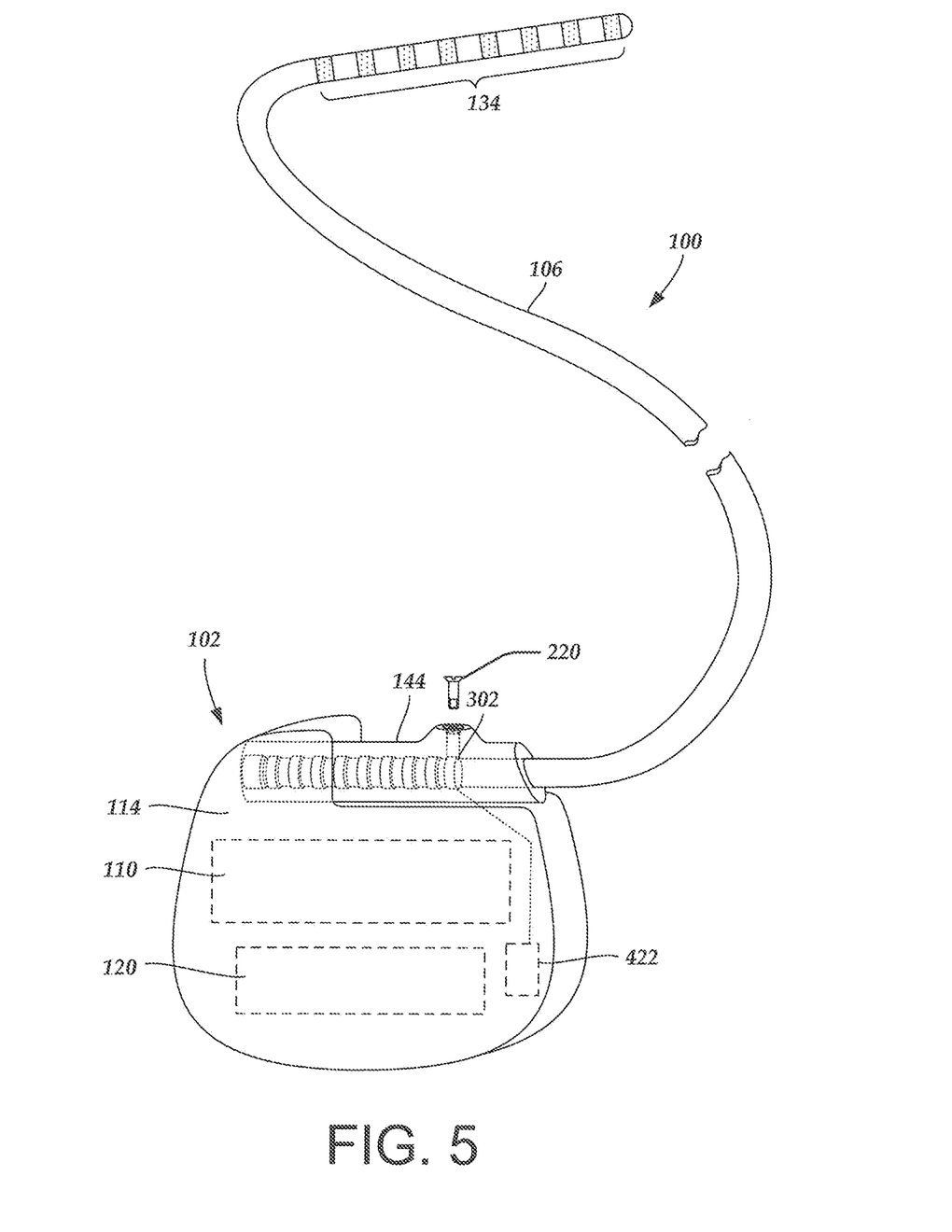
FIG. 5 Is a schematic perspective view of yet another embodiment of an electrical stimulation system, according to the invention.

FIG. 5 illustrates another embodiment in which the diversionary terminal contact 302 acts as a retention sleeve against which a retention fastener 220 (e.g., a screw) can be tightened to hold the lead within the connector of the control module. In some embodiments, the retention fastener may conduct current for dissipation into surrounding tissue, optionally, through a conductive portion of the housing of the control module which is in electrical communication with the retention fastener.

It will be understood that stimulation system 100 can include more, fewer, or different components, and can have a variety of different configurations known to those skilled in the art. For example, instead of lead 106, the electrodes 118 can be disposed in an array at or near the distal end of lead and form a paddle lead (not shown). A paddle lead may be a flat structure along the length of the lead.

Embodiments of the present disclosure may be used in any medical or non-medical procedure, including any medical procedure where one or more body part requires electrical stimulation. The invention may also apply to any device containing a relatively long element with conductive paths (e.g. leads) in applications that include but are not limited to neurostimulators, cardiac stimulators, and cochlear implants. In addition, at least certain aspects of the aforementioned embodiments may be combined with other aspects of the embodiments, or removed, without departing from the scope of the present disclosure.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An implantable lead, comprising:
   a lead body having a proximal end and a distal end;
   a plurality of electrodes disposed along the distal end of the lead body;
   a plurality of terminal contacts disposed along the proximal end of the lead body;
   a plurality of stimulation conductors extending along the lead body and electrically coupling the plurality of electrodes to the plurality of terminal contacts;
   at least one diversionary terminal contact disposed along the proximal end of the lead body; and
   at least one diversionary conductor, disposed within the lead body, extending at least partially along the length of the lead body, conductively attached directly and solely to a one of the at least one diversionary terminal contact, and not coupled to any of the electrodes, wherein the at least one diversionary conductor is configured and arranged to capacitively couple to the stimulation conductors and each diversionary conductor is a single wire that presents a lower impedance to RF energy at a preselected MRI frequency than any of the stimulation conductors.

2. The lead of claim 1, wherein the at least one diversionary conductor is configured and arranged to capacitively couple RF energy from the stimulation conductors when RF energy from an MRI procedure impinges on the lead.

3. The lead of claim 1, wherein the at least one diversionary conductor extends parallel to the plurality of stimulation conductors.

4. The lead of claim 1, wherein the at least one diversionary conductor is wound around at least a portion of at least one of the plurality of stimulation conductors.

5. The lead of claim 1, wherein the at least one diversionary conductor comprises a plurality of diversionary conductors.

6. The lead of claim 5, wherein the plurality of diversionary conductors each have a different length.

7. The lead of claim 6, wherein the length of each of the plurality of diversionary conductors corresponds to an integer multiple of one half of a wavelength of a different one of a characteristic MRI RF frequency.

8. The lead of claim 1, wherein a length of at least one of the at least one diversionary conductor corresponds to an integer multiple of one half of a wavelength of characteristic MRI RF frequency.

9. An implantable stimulation system, comprising:
an implantable lead comprising
a lead body having a proximal end and a distal end,
a plurality of electrodes disposed along the distal end of the lead body,
a plurality of terminal contacts disposed along the proximal end of the lead body;
a plurality of stimulation conductors extending along the lead body and electrically coupling the plurality of electrodes to the plurality of terminal contacts,
at least one diversionary terminal contact disposed along the proximal end of the lead body, and
at least one diversionary conductor, disposed within the lead body, extending at least partially along the length of the lead body, conductively attached directly and solely to a one of the at least one diversionary terminal contact, and not coupled to any of the electrodes, wherein the at least one diversionary conductor is configured and arranged to capacitively couple to the stimulation conductors and each diversionary conductor is a single wire that presents a lower impedance to RF energy at a preselected MRI frequency than any of the stimulation conductors; and
a control module comprising
a housing,
stimulation electronics disposed within the housing of the control module,
a connector configured and arranged to receive the proximal end of the lead,
a plurality of conductive contacts disposed within the connector and configured and arranged for contacting the plurality of terminal contacts of the lead and coupling the lead to the stimulation electronics, and
at least one diversionary conductive contact disposed within the connector and configured and arranged for contacting the at least one diversionary terminal contact of the lead.

10. The system of claim 9, wherein the at least one diversionary conductor extends parallel to the plurality of stimulation conductors.

11. The system of claim 9, wherein the at least one diversionary conductor is wound around a portion of at least one of the plurality of stimulation conductors.

12. The system of claim 9, wherein the at least one diversionary conductors comprises a plurality of diversionary conductors.

13. The system of claim 9, wherein the plurality of diversionary conductors each have a different length.

14. The system of claim 9, wherein the control module further comprises a retention fastener disposed in the connector and configured and arranged to fasten against at least one of the at least one diversionary terminal contact of the lead.

15. The system of claim 9, wherein the housing of the control module comprises an exterior conductive portion and wherein the at least one diversionary contact of the connector is electrically coupled to the exterior conductive portion.

16. The system of claim 9, wherein the control module further comprises at least one component electrically coupled to the at least one diversionary contact of the connector and the at least one component is configured and arranged to dissipate or store current directed to the at least one component from the at least one diversionary contact of the connector.

17. An implantable stimulation system, comprising:
i) an implantable lead comprising
a lead body having a proximal end and a distal end,
a plurality of electrodes disposed along the distal end of the lead body,
a plurality of terminal contacts disposed along the proximal end of the lead body;
a plurality of stimulation conductors extending along the lead body and electrically coupling the plurality of electrodes to the plurality of terminal contacts,
at least one diversionary terminal contact disposed along the proximal end of the lead body, and
at least one diversionary conductor, disposed within the lead body, extending at least partially along the length of the lead body, conductively attached directly and solely to a one of the at least one diversionary terminal contact, and not coupled to any of the electrodes, wherein the at least one diversionary conductor is configured and arranged to capacitively couple to the stimulation conductors and each diversionary conductor is a single wire that presents a lower impedance to RF energy at a preselected MRI frequency than any of the stimulation conductors;
ii) an implantable lead extension having a proximal end and a distal end and comprising
a connector disposed at the distal end of the lead extension and configured and arranged to receive the proximal end of the lead,
a plurality of conductive contacts disposed within the connector and configured and arranged for contacting the plurality of terminal contacts of the lead,
at least one diversionary conductive contact disposed within the connector and configured and arranged for contacting the at least one diversionary terminal contact of the lead,
a plurality of terminal contacts disposed along the proximal end of the lead extension;
at least one diversionary terminal contact disposed along the proximal end of the lead extension, and
a plurality of conductors extending along the lead extension and electrically coupling the plurality of conductive contacts to the plurality of terminal contacts and the at least one diversionary conductive contact to the at least one diversionary terminal contact; and
iii) a control module comprising
stimulation electronics disposed within the control module,
a connector configured and arranged to receive the proximal end of the lead extension,
a plurality of conductive contacts disposed within the connector and configured and arranged for contacting the plurality of terminal contacts of the lead extension and coupling the lead and lead extension to the stimulation electronics, and
at least one diversionary conductive contact disposed within the connector and configured and arranged for contacting the at least one diversionary terminal contact of the lead extension.

18. The system of claim 17, wherein the housing of the control module comprises an exterior conductive portion and wherein the at least one diversionary contact of the connector is electrically coupled to the exterior conductive portion.

19. The system of claim 17, wherein the control module further comprises at least one component electrically coupled to the at least one diversionary contact of the connector and configured and arranged to dissipate or store current directed to the at least one component from the at least one diversionary contact of the connector.

20. The system of claim 17, wherein a length of at least one of the ate least one diversionary conductor corresponds to an integer multiple of one half of a wavelength of characteristic MRI frequency.

* * * * *